United States Patent
Beckman et al.

(10) Patent No.: US 8,231,527 B2
(45) Date of Patent: Jul. 31, 2012

(54) ROLL-UP WOUND PROTECTOR WITH ASYMMETRIC RING

(75) Inventors: Andrew T. Beckman, Cincinnati, OH (US); Chester O. Baxter, III, Loveland, OH (US); Carrie I. Fihe, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 409 days.

(21) Appl. No.: 11/458,328

(22) Filed: Jul. 18, 2006

(65) Prior Publication Data

US 2008/0021359 A1    Jan. 24, 2008

(51) Int. Cl.
*A61B 1/32*    (2006.01)

(52) U.S. Cl. .................. 600/208; 600/206; 600/207

(58) Field of Classification Search .......... 600/206–208; 602/75; 128/856
See application file for complete search history.

(56) References Cited

U.S. PATENT DOCUMENTS

| | | | |
|---|---|---|---|
| 563,645 A | 7/1896 | Bitting | |
| 2,739,587 A | 3/1956 | Scholl | |
| 3,111,943 A | 11/1963 | Orndorff | |
| 3,332,417 A | 7/1967 | Blanford et al. | |
| 3,347,226 A | 10/1967 | Harrower | |
| 3,347,227 A | 10/1967 | Harrower | |
| 3,397,692 A | 8/1968 | Creager, Jr. et al. | |
| 4,881,939 A * | 11/1989 | Newman | 600/31 |
| 4,995,381 A * | 2/1991 | Marmar et al. | 600/39 |
| 5,292,330 A | 3/1994 | Shutt | |
| 5,324,268 A | 6/1994 | Yoon | |
| 5,337,754 A * | 8/1994 | Heaven et al. | 600/562 |
| 5,366,478 A | 11/1994 | Brinkerhoff et al. | |
| 5,437,683 A | 8/1995 | Neumann et al. | |
| 5,441,707 A * | 8/1995 | Lewis et al. | 422/300 |
| 5,460,170 A | 10/1995 | Hammerslag | |
| 5,480,410 A | 1/1996 | Cuschieri et al. | |
| 5,514,133 A | 5/1996 | Golub et al. | |
| 5,522,791 A | 6/1996 | Leyva | |
| 5,524,644 A | 6/1996 | Crook | |
| 5,526,536 A | 6/1996 | Cartmill | |
| 5,545,179 A | 8/1996 | Williamson, IV | |
| 5,640,977 A | 6/1997 | Leahy et al. | |
| 5,649,550 A | 7/1997 | Crook | |
| 5,653,705 A | 8/1997 | De La Torre et al. | |
| 5,653,717 A | 8/1997 | Ko et al. | |
| 5,672,168 A | 9/1997 | De La Torre et al. | |
| 5,741,298 A | 4/1998 | MacLeod | |
| 5,803,921 A | 9/1998 | Bonadio | |
| 5,810,721 A | 9/1998 | Mueller et al. | |

(Continued)

FOREIGN PATENT DOCUMENTS

EP    0887047 A1    12/1998

(Continued)

*Primary Examiner* — Eduardo C Robert
*Assistant Examiner* — Julianna N Harvey

(57) ABSTRACT

A roll-up wound protector has a distal ring, a proximal ring, and a flexible sleeve extending between the proximal and distal rings. The proximal ring is rollable to gather the flexible sleeve around the proximal ring and shorten the length of the flexible sleeve. The cross-sectional geometry of the proximal ring may be generally s-shaped. The cross-sectional geometry may be asymmetric about the longitudinal axis and asymmetric about the lateral axis. The height along the longitudinal axis may be greater than the width along the lateral axis. The proximal ring may comprise a medial surface having a circumferential recess and a lateral surface having a circumferential recess, the two recesses being longitudinally staggered relative one another.

13 Claims, 3 Drawing Sheets

U.S. PATENT DOCUMENTS

| | | | |
|---|---|---|---|
| 5,813,409 A | 9/1998 | Leahy et al. | |
| 5,853,395 A * | 12/1998 | Crook et al. | 604/174 |
| 5,899,208 A | 5/1999 | Bonadio | |
| 5,906,577 A | 5/1999 | Beane et al. | |
| 5,925,064 A | 7/1999 | Meyers et al. | |
| 5,947,922 A | 9/1999 | MacLeod | |
| 5,957,913 A | 9/1999 | De La Torre et al. | |
| 6,024,736 A | 2/2000 | De La Torre et al. | |
| 6,033,426 A | 3/2000 | Kaji | |
| 6,033,428 A | 3/2000 | Sardella | |
| 6,048,309 A | 4/2000 | Flom et al. | |
| 6,110,154 A | 8/2000 | Shimomura et al. | |
| 6,142,935 A | 11/2000 | Flom et al. | |
| 6,142,936 A | 11/2000 | Beane et al. | |
| 6,149,642 A | 11/2000 | Gerhart et al. | |
| 6,158,437 A * | 12/2000 | Vagley | 128/898 |
| 6,159,200 A | 12/2000 | Verdura et al. | |
| 6,165,184 A | 12/2000 | Verdura et al. | |
| 6,228,022 B1 | 5/2001 | Friesem et al. | |
| 6,254,534 B1 | 7/2001 | Butler et al. | |
| 6,312,258 B1 * | 11/2001 | Ashman | 433/172 |
| 6,315,770 B1 | 11/2001 | De La Torre et al. | |
| 6,319,246 B1 | 11/2001 | De La Torre et al. | |
| 6,382,211 B1 | 5/2002 | Crook | |
| 6,440,063 B1 | 8/2002 | Beane et al. | |
| 6,450,983 B1 * | 9/2002 | Rambo | 602/60 |
| 6,485,467 B1 | 11/2002 | Crook et al. | |
| 6,578,577 B2 | 6/2003 | Bonadio et al. | |
| 6,582,364 B2 | 6/2003 | Butler et al. | |
| 6,589,167 B1 | 7/2003 | Shimomura et al. | |
| 6,613,952 B2 | 9/2003 | Rambo | |
| 6,623,426 B2 | 9/2003 | Bonadio et al. | |
| 6,676,706 B1 | 1/2004 | Mears et al. | |
| 6,723,044 B2 * | 4/2004 | Pulford et al. | 600/208 |
| 6,814,078 B2 | 11/2004 | Crook | |
| 6,814,700 B1 | 11/2004 | Mueller et al. | |
| 6,846,287 B2 | 1/2005 | Bonadio et al. | |
| 2001/0037053 A1 | 11/2001 | Bonadio et al. | |
| 2001/0047188 A1 | 11/2001 | Bonadio et al. | |
| 2002/0002324 A1 | 1/2002 | McManus | |
| 2002/0010389 A1 | 1/2002 | Butler et al. | |
| 2002/0038077 A1 | 3/2002 | De La Torre et al. | |
| 2002/0068923 A1 | 6/2002 | Caldwell et al. | |
| 2002/0072762 A1 | 6/2002 | Bonadio et al. | |
| 2002/0162559 A1 | 11/2002 | Crook | |
| 2002/0183594 A1 | 12/2002 | Beane et al. | |
| 2003/0062051 A1 | 4/2003 | Rambo | |
| 2003/0078478 A1 | 4/2003 | Bonadio et al. | |
| 2003/0187376 A1 | 10/2003 | Rambo | |
| 2003/0192553 A1 * | 10/2003 | Rambo | 128/850 |
| 2004/0015185 A1 | 1/2004 | Ewers et al. | |
| 2004/0049099 A1 | 3/2004 | Ewers et al. | |
| 2004/0049100 A1 | 3/2004 | Butler et al. | |
| 2004/0073090 A1 | 4/2004 | Butler et al. | |
| 2004/0092795 A1 | 5/2004 | Bonadio et al. | |
| 2004/0092796 A1 | 5/2004 | Butler et al. | |
| 2004/0097793 A1 | 5/2004 | Butler et al. | |
| 2004/0127772 A1 | 7/2004 | Ewers et al. | |
| 2004/0154624 A1 | 8/2004 | Bonadio et al. | |
| 2004/0249248 A1 | 12/2004 | Bonadio et al. | |
| 2004/0254426 A1 | 12/2004 | Wenchell | |
| 2004/0260153 A1 | 12/2004 | Pulford et al. | |
| 2004/0267096 A1 | 12/2004 | Caldwell et al. | |
| 2005/0020884 A1 | 1/2005 | Hart et al. | |
| 2005/0241647 A1 * | 11/2005 | Nguyen et al. | 128/856 |

FOREIGN PATENT DOCUMENTS

| | | |
|---|---|---|
| EP | 0887048 A1 | 12/1998 |
| EP | 0888755 A1 | 1/1999 |
| EP | 0776180 B1 | 1/2000 |
| EP | 1000583 B1 | 5/2003 |
| EP | 1312318 A1 | 5/2003 |
| EP | 0845960 B1 | 4/2004 |
| EP | 1415610 A2 | 5/2004 |
| EP | 1415610 A3 | 5/2004 |
| EP | 1442710 A1 | 8/2004 |
| EP | 1135070 B1 | 9/2004 |
| WO | WO 9311811 A1 | 6/1993 |
| WO | WO 95/22289 A2 | 8/1995 |
| WO | WO 95/24864 A1 | 9/1995 |
| WO | WO 95/27468 A1 | 10/1995 |
| WO | WO 96/10963 A1 | 4/1996 |
| WO | WO 9707742 A1 | 3/1997 |
| WO | WO 9848724 A1 | 11/1998 |
| WO | WO 9903416 A1 | 1/1999 |
| WO | WO 9925268 A1 | 5/1999 |
| WO | WO 0024326 A2 | 5/2000 |
| WO | WO 0032116 A1 | 6/2000 |
| WO | WO 0032117 A1 | 6/2000 |
| WO | WO 0032120 A1 | 6/2000 |
| WO | WO 0054676 A1 | 9/2000 |
| WO | WO 0054677 A1 | 9/2000 |
| WO | WO 0108581 A2 | 2/2001 |
| WO | WO 0126558 A1 | 4/2001 |
| WO | WO 0234108 A2 | 5/2002 |
| WO | WO 03028523 A2 | 4/2003 |
| WO | WO 03077726 A2 | 9/2003 |
| WO | WO 03/103548 A1 | 12/2003 |
| WO | WO 2004026153 A1 | 4/2004 |
| WO | WO 2004030547 A1 | 4/2004 |
| WO | WO 2004054456 A1 | 7/2004 |
| WO | WO 2004075730 A2 | 9/2004 |
| WO | WO 2004075741 A2 | 9/2004 |
| WO | WO 2004/096012 A2 | 11/2004 |
| WO | WO 2004103161 A2 | 12/2004 |

* cited by examiner

FIG. 4
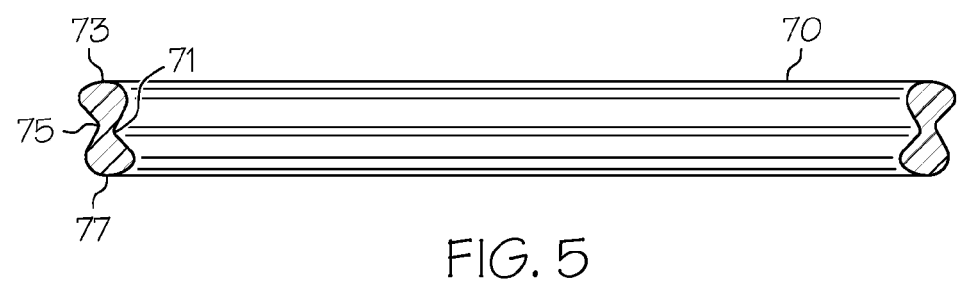
FIG. 5
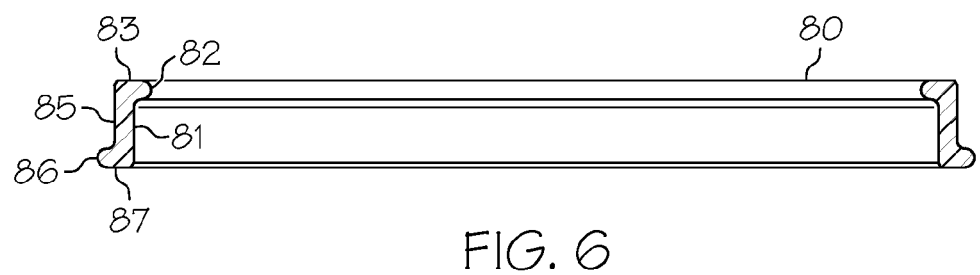
FIG. 6
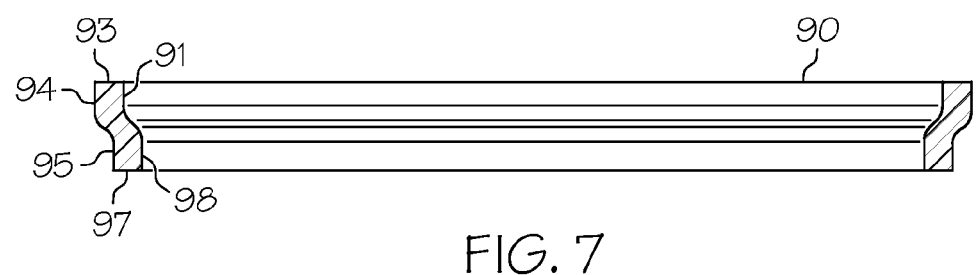
FIG. 7
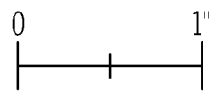

ROLL-UP WOUND PROTECTOR WITH ASYMMETRIC RING

BACKGROUND

The present invention relates in general to surgical devices and procedures, and more particularly to wound protectors and wound retractors.

Surgical procedures are often used to treat and cure a wide range of diseases, conditions, and injuries. Many surgical procedures require access to internal tissue through open surgical procedures or endoscopic surgical procedures. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Trocars are often used to provide a port through which endoscopic surgical instruments are passed. Trocars generally have a sealing valve that prevent the insufflatory fluid from escaping while an instrument is positioned in the trocar. Sometimes hand access devices are also used during endoscopic surgery, often referred to as hand assisted laparoscopic surgery ("HALS"). A HALS device will typically seal around a surgeon's hand or arm to prevent the insufflatory fluid from escaping while allowing the surgeon to manipulate tissue within the patient's body.

While wound protectors and wound retractors are known, no one has previously made or used a wound protector or wound retractor in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are drawn to scale and like reference numerals identify the same elements.

FIG. 4 depicts a cross-sectional view of a proximal ring;

FIG. 5 depicts a cross-sectional view of a proximal ring;

FIG. 6 depicts a cross-sectional view of a proximal ring; and

FIG. 7 depicts a cross-sectional view of a proximal ring.

DETAILED DESCRIPTION

Figure 1:
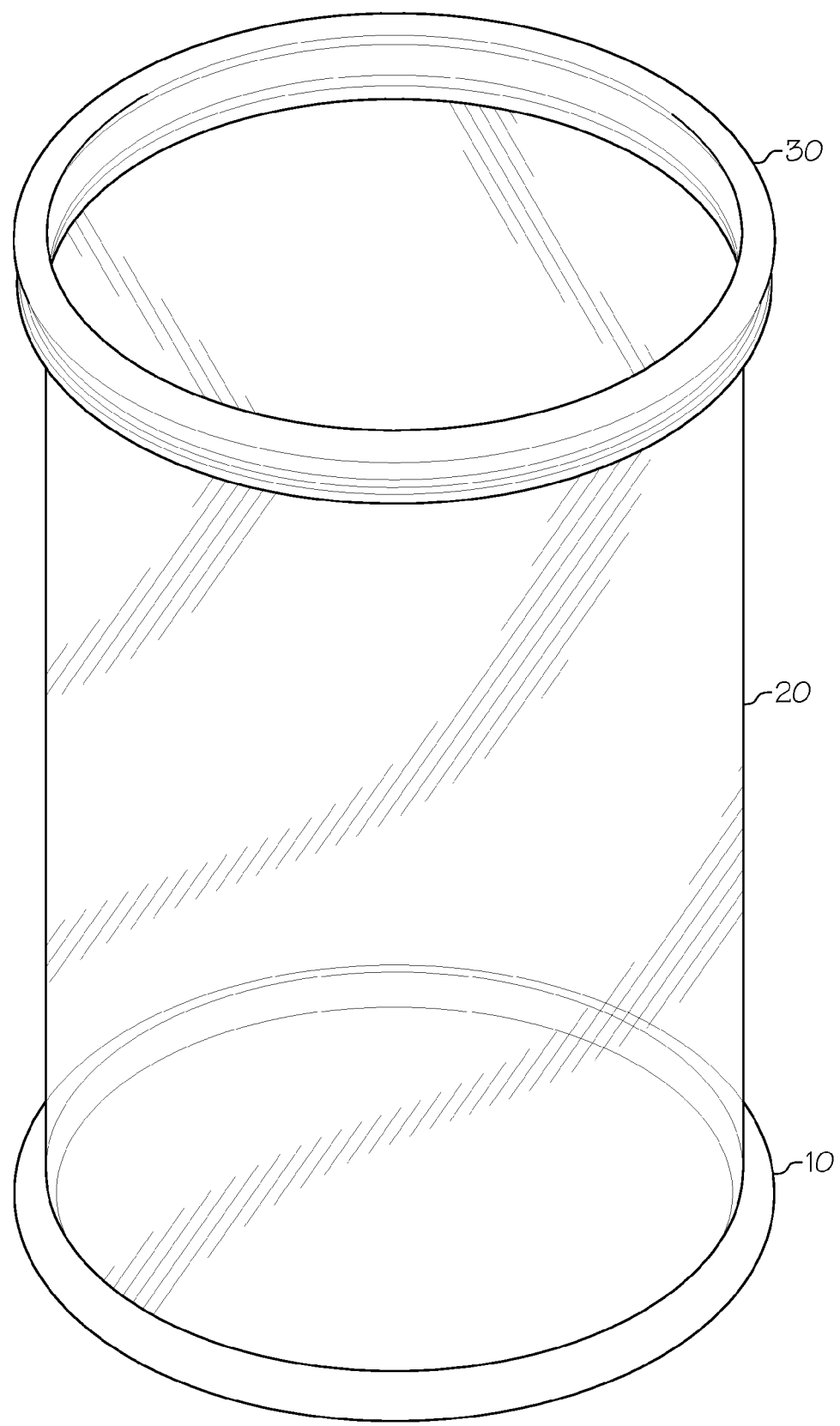
FIG. 1 depicts an non-scaled schematic view of a roll-up wound protector.

FIG. 1 depicts a perspective view of a roll-up wound protector in an extended position. The wound protector comprises a distal ring (10), a proximal ring (30), and a flexible sleeve (20) having a length extending between the proximal and distal rings. The wound protector can be used as a stand-alone device or in combination with a cap having sealing valve for endoscopic instruments or a surgeon's arm.

In this embodiment the distal ring (10) is circular with a circular cross-sectional geometry; however, non-circular rings and non-circular cross-sectional geometries are also possible. For instance, the distal ring could have a oval or elliptical in cross-sectional shape. The distal ring (10) can be made from a variety of different materials with different characteristics. In this example the distal ring is made from an elastomer such as polyurethane, polyethylene, silicone, and the like. The distal ring can also vary in size. For instance, the distal ring can have an inside diameter greater than 1 inches and less than 9 inches, and a thickness less than 1 inch, but dimensions outside these ranges are also possible. Optionally, the distal ring (10) will have a durometer between 40 A and 90 A or 70 D, but other material properties are also possible.

In this embodiment the sleeve (20) is a single layered tube of material; however, a discontinuous sleeve or multi-layered sleeves are also possible. The sleeve (20) can be made from a variety of variety of different materials with different characteristics. In one example, the sleeve (20) is made from an elastomer such as polyisoprene, silicone, polyurethane, silicone, and the like; however, inelastic materials such as mylar could also be used. The sleeve (20) may be clear, transparent, translucent, or opaque. As shown here, the sleeve (20) is fastened at its ends directly to the proximal and distal rings using an adhesive or heat sealing techniques; however, alternative techniques may also be employed. The sleeve (20) could also be attached to the rings at locations other than the sleeve ends. For instance, the sleeve (20) can wrapped around the distal ring (10) and adhesively attached or sealed to itself. The length of the sleeve (20) can also vary. For instance, the sleeve may be between 2 cm and 20 cm in length; however, other lengths are also possible. The thickness of the sleeve (20) can also vary. For instance, the sleeve thickness in this embodiment is between 0.010 and 0.020 inches; however, other thicknesses are also possible.

In this embodiment the proximal ring (30) is circular; however, non-circular rings are also possible. The proximal ring (30) can also vary in size. For instance, the proximal ring (30) can have an inside diameter between 1 and 9 inches, but other dimensions are also possible. Optionally, the ratio of the distal ring (10) and proximal ring (30) diameters is greater than 0.4. The proximal ring (30) in this example has a generally s-shaped cross-sectional geometry with a height greater than the width. In this embodiment, the cross-sectional geometry is substantially constant around the circumference of the proximal ring (30). A geometry is substantially constant if any variations are insignificant. For example, geometric variations resulting only from molding or other manufacturing factors would be considered substantially constant. Also in this embodiment the cross-sectional geometry is substantially solid; however, holes or cavities may also be present.

Figure 2:
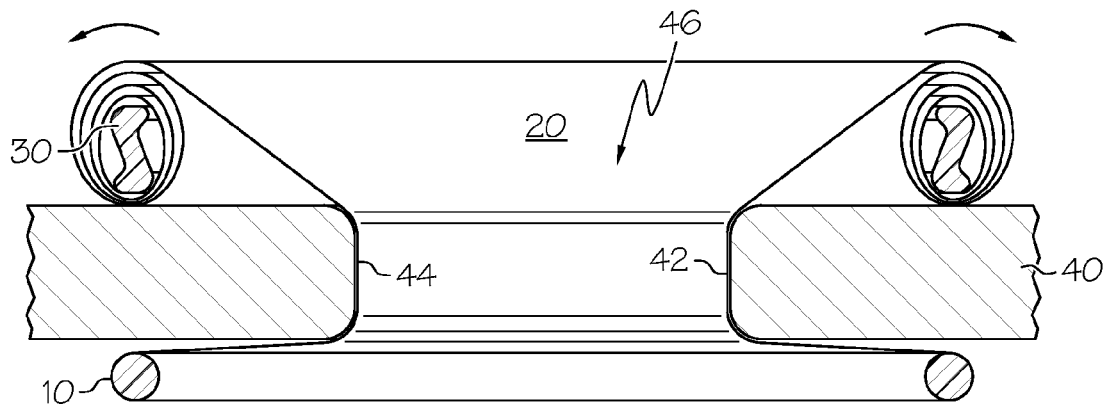
FIG. 2 depicts a non-scaled schematic view of a roll-up wound protector deployed in an abdomen.

FIG. 2 depicts an example of the wound protector in a deployed position in a patient. In this example the wound protector in positioned in a patient's abdominal wall (40) through an incision (46). The distal ring (10) is held in a collapsed position (e.g., in an oblong shape like an oval, a peanut, a figure eight, and the like) to reduce its size and then inserted through the incision (46). After insertion, the distal ring (10) is released and then expands to its ring-like shape. As shown here, the expanded distal ring (10) is larger than the incision (46) and sits against the peritoneal surface of the abdominal wall (40). The proximal ring (30) is rollable to gather the flexible sleeve (20) around the proximal ring (30), and the wound proximal ring (30) sits on the cutaneous surface of the abdominal wall (40). The proximal ring (30) is rollable in the outward directions (as shown by the arrows) to shorten the sleeve (20) and in the inward direction to lengthen the sleeve (20), or vice versa. The shortening of the sleeve (20) pulls the sleeve (20) taut against the incised wound (42, 44). As one with ordinary skill in the art will recognize, surgical procedures can be performed through the incision (46) and the sleeve (20) protects the incised wound (42,44) from infection and contamination. In addition, the taut sleeve (20) tends to pull the incised wound (42,44) open thus functioning as a wound retractor. As demonstrated in this example, more retraction is possible by rolling the proximal ring (30) outward, while less retraction is possible by rolling the proximal ring (30) inward.

In this example the proximal ring (30) rolls in resting increments of 180 degrees. In other words, when the ring rolls it "snaps" between resting positions. Optionally, the flip force for the proximal ring (30) can be less 10 in*lbs/180 degrees of rotation, and can be less than 3 in*lbs. Flip force is a way of measuring the force required to roll the ring about itself. The flip force is measured at room temperature on a stand-alone proximal ring without the sleeve attached. An equal and opposite torque is applied simultaneously to a ring at two diametrically opposite points along the circumference of the ring. The peak measured torque to roll the ring is used to calculate the flip force. By compiling 100 peak measured torques for a given ring, the statistical median value is the flip force. Preferably, the flip force is substantially the same for each sequential resting incremental rotation. Optionally, the proximal ring (30) may have substantially no residual hoop stress. One way to achieve this is through a molding process where the proximal ring (30) is injection molded and transfer molded using a thermoplastic or thermoset elastomer such as polyisoprene, silicone, polyurethane, silicone, and the like. In one embodiment, the proximal ring is molded from Desmopan 9370. The proximal ring (30) may have a durometer between 50 A and 50 D, but other material properties are also possible.

Figure 3:
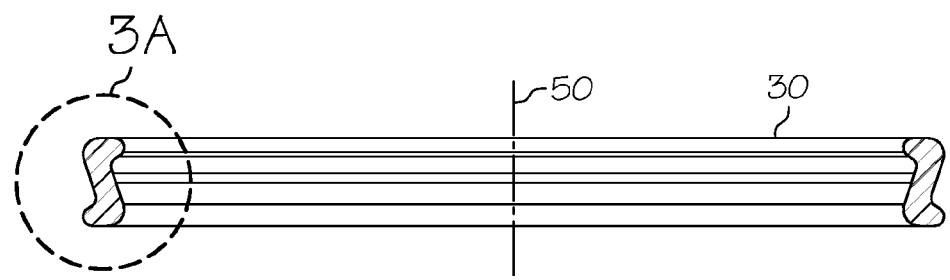
FIG. 3 depicts a cross-sectional view of a proximal ring.
Figure 3A:
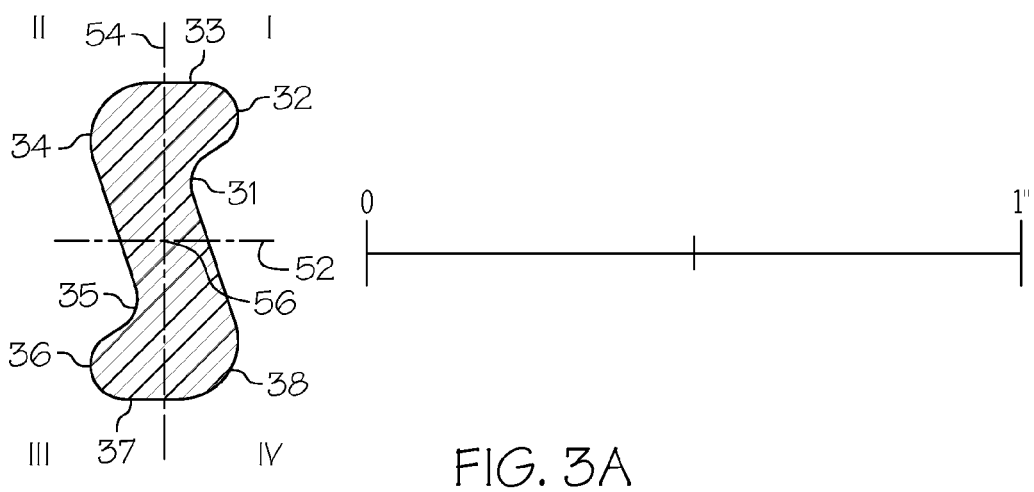
FIG. 3A depicts more detailed cross-sectional view from FIG. 3.

FIGS. 3 and 3A illustrate an example of a cross-sectional geometry of the proximal ring (30). The proximal ring (30) comprises a central axis (50). A longitudinal axis (54) is parallel to the central axis (50) and crosses the centroid (56) of the cross-sectional geometry. A lateral axis (52) is normal to the central axis (50) and also crosses the centroid (56). The axes (52, 54) define four quadrants (I, II, III, IV). In this embodiment the height along the longitudinal axis (54) is greater than the width along the lateral axis (52). The cross-sectional shape shown in these figures is asymmetric about the longitudinal axis (54) and asymmetric about the lateral axis (52). In addition, the cross-sectional shape in this embodiment is symmetric between each pair of diagonal quadrants. In other words, the cross-sectional shapes in quadrants I and III are symmetric and the cross-sectional shapes in quadrants II and IV are symmetric. Two diagonal quadrants are symmetric if a quadrant is rotated 180 degrees about the centroid (56) and the cross-sectional shapes of the two quadrants are substantially the same. Shapes are substantially the same if any variations are insignificant. For example, geometric variations resulting from molding or other manufacturing factors would be considered substantially the same.

The surfaces are substantially constant about the circumference of the proximal ring (30). In the present embodiment the various surfaces transition smoothly, but geometric abrupt transitions are also possible. The medial surface includes a concave arcuate recess (31) that transitions to a convex arcuate expansion (32). The expansion (32) transitions to proximal surface (33), shown here as a flat normal the longitudinal axis (54). The proximal surface (33) transitions to a lateral surface comprising a convex arcuate expansion (34), which transitions to a concave arcuate recess (35), then to a convex arcuate expansion (36), then to a distal surface (37), shown here as a flat normal the longitudinal axis (54). The distal surface (37) transitions to the medial convex arcuate expansion (38), which then transitions to the concave arcuate recess (31). In this embodiment the recesses (31, 35) are longitudinally staggered to each other, the medial recess (31) being proximal the lateral recess (35).

FIG. 4 illustrates another example of a cross-sectional geometry of a proximal ring (60). The cross-sectional geometry is generally s-shaped and includes a centroid, a longitudinal axis, and a lateral axis. In this embodiment the height along the longitudinal axis is greater than the width along the lateral axis. The cross-sectional shape is asymmetric about the longitudinal axis and asymmetric about the lateral axis. In addition, the cross-sectional shape is symmetric between each pair of diagonal quadrants. The surfaces transition smoothly and are substantially constant about the circumference of the proximal ring (60). In this embodiment the medial and lateral concave recesses (61, 65) are longitudinally staggered to each other, the medial recess (61) being proximal the lateral recess (65). The proximal and distal surfaces (63, 67) are shown as flats at acute angles relative the longitudinal axis.

FIG. 5 illustrates yet another example of a cross-sectional geometry of a proximal ring (70). The cross-sectional geometry is generally s-shaped and includes a centroid, a longitudinal axis, and a lateral axis. In this embodiment the height along the longitudinal axis is greater than the width along the lateral axis. The cross-sectional shape is asymmetric about the longitudinal axis and asymmetric about the lateral axis. In addition, the cross-sectional shape is symmetric between each pair of diagonal quadrants. The surfaces transition smoothly and are substantially constant about the circumference of the proximal ring (70). In this embodiment the medial and lateral concave recesses (71, 75) are longitudinally staggered to each other, the medial recess (71) being distal the lateral recess (75). The proximal and distal surface (73, 77) are shown as arcuate convex surfaces.

FIG. 6 illustrates still another example of a cross-sectional geometry of a proximal ring (80). The cross-sectional geometry includes a centroid, a longitudinal axis, and a lateral axis. In this embodiment the height along the longitudinal axis is greater than the width along the lateral axis. The cross-sectional shape is asymmetric about the longitudinal axis and asymmetric about the lateral axis. In addition, the cross-sectional shape is symmetric between each pair of diagonal quadrants. The surfaces are substantially constant about the circumference of the proximal ring (80). In this embodiment the medial surface includes a flat portion (81) parallel the longitudinal axis that transitions to convex arcuate expansion (82). The expansion (82) transitions to proximal surface (83), shown here as a flat normal the longitudinal axis. The proximal surface (83) transitions to a lateral surface comprising a flat portion (85) parallel the longitudinal axis that transitions to convex arcuate expansion (86), then to a distal surface (87), shown here as a flat normal the longitudinal axis. The distal surface (87) transitions to the medial flat portion (81). The various surfaces may transition smoothly through radiuses or more dramatically through chamfers or sharp angles. In this embodiment the flat portions (81, 85) are longitudinally staggered to each other, the medial flat portion (81) being distal the lateral flat portion (85).

FIG. 7 illustrates another example of a cross-sectional geometry of a proximal ring (90). The cross-sectional geometry includes a centroid, a longitudinal axis, and a lateral axis. In this embodiment the height along the longitudinal axis is greater than the width along the lateral axis. The cross-sectional shape is asymmetric about the longitudinal axis and asymmetric about the lateral axis. In addition, the cross-sectional shape is symmetric between each pair of diagonal quadrants. The surfaces are substantially constant about the circumference of the proximal ring (90). In this embodiment the medial surface includes a flat expansion portion (98) parallel the longitudinal axis that transitions smoothly to a flat recess portion (91). The recess (91) transitions to proximal surface (93), shown here as a flat normal the longitudinal axis. The proximal surface (93) transitions to a lateral surface comprising a flat expansion portion (94) parallel the longitudinal axis that transitions smoothly to a flat recess portion (95) parallel the longitudinal axis, then to a distal surface (97), shown here as a flat normal the longitudinal axis. The distal surface (97) transitions to the medial expansion portion (98). In this embodiment the recesses (91, 95) are longitudinally staggered to each other, the medial recess (91) being proximal the lateral recess (95).

Preferably, the wound protectors described above will be processed before surgery. First, a new or used wound protector is obtained and if necessary cleaned. The wound protector can then be sterilized. In one sterilization technique the wound protector is placed in a closed and sealed container, such as a plastic or TYVEK bag. Optionally, the wound protector can be bundled in the container as a kit with other components, including one or more of the following: a sealing cap to maintain pneumoperitoneum, a sealing cap with a valve to allow passage of surgical instruments or a surgeon's arm while maintaining pneumoperitoneum (e.g., iris valve, gel seal, cuff, and the like), a tube of lubricant, a mounting ring in which the proximal ring may be seated and to which a cap can be attached, a marker, an incision template or scale, an instruction sheet, and the like. The container and wound protector, as well as any other components, are then placed in a field of radiation that can penetrate the container, such as gamma radiation, x-rays, or high-energy electrons. The radiation kills bacteria on the wound protector and in the container. The sterilized wound protector can then be stored in the sterile container. The sealed container keeps the wound protector sterile until it is opened in the medical facility.

The wound protectors described above can be used as a stand-alone device, for instance in open surgical procedures, or in combination with a cap having sealing valve for endoscopic instruments or a surgeon's arm. Among other advantages, the foregoing examples provide effective wound protection to prevent infection and facilitate wound retraction. Because the sleeve rolls-up, its length can be adjusted by the surgeon for any given anatomy and patient. Further, the surgeon can select the amount of retraction desired for a given procedure. The cross-sectional shapes of the proximal ring are easy to grip thus facilitating ease of use. Furthermore, the flip forces are relatively low and constant, further facilitating ease of use.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical wound protector having a fully extended configuration and a gathered configuration, the wound protector comprising:
   a) a distal ring;
   b) a proximal ring comprising a central axis and a cross-sectional geometry, the cross-sectional geometry comprising
      (i) a centroid, a longitudinal axis parallel to the central axis and crossing the centroid when the wound protector is in the fully extended configuration, and a lateral axis normal to the central axis and crossing the centroid when the wound protector is in the fully extended configuration;
      (ii) a shape being asymmetric about the longitudinal axis and asymmetric about the lateral axis;
      (iii) a height along the longitudinal axis and a width along the lateral axis as measured when the wound protector is in the fully extended configuration, the height being greater than the width; and
   c) a flexible sleeve having a length extending between the proximal and distal rings;
   wherein the proximal ring is rollable to gather the flexible sleeve around the proximal ring and shorten the length of the flexible sleeve from the fully extended configuration to a gathered configuration.

2. The surgical wound protector of claim 1, wherein the cross-sectional geometry is solid.

3. The surgical wound protector of claim 1, wherein the cross-sectional geometry is generally s-shaped.

4. The surgical wound protector of claim 1, wherein the cross-sectional geometry is substantially constant around the proximal ring.

5. The surgical wound protector of claim 1, wherein the proximal ring has substantially no residual hoop stress.

6. The surgical wound protector of claim 1, wherein the proximal ring rolls in resting increments of 180 degrees.

7. The surgical wound protector of claim 6, wherein the flip force for the proximal ring is less than 3 in*lbs.

8. The surgical wound protector of claim 6, wherein the flip force for the proximal ring is substantially the same for each incremental rotation.

9. The surgical wound protector of claim 1, wherein the longitudinal axis and lateral axis define four quadrants, the shape of the cross-sectional geometry being symmetric between each pair of diagonal quadrants.

10. A surgical wound protector, comprising:
    a) a distal ring;
    b) a proximal ring extending about a central ring axis, the proximal ring having a proximal ring cross-section having a centroid, a longitudinal axis extending through the centroid and extending substantially parallel to the central ring axis, and a lateral axis extending through the centroid and substantially perpendicular to the longitudinal axis,
    wherein the proximal ring cross section is asymmetric about any axis extending through the centroid in the plane of the cross-section axis, and wherein the proximal ring comprises a medial surface having a single continuous circumferential recess and a lateral surface having a single continuous circumferential recess, the two recesses being longitudinally staggered relative one another; and
    c) a flexible sleeve extending between the proximal and distal rings;

wherein the proximal ring is rollable to gather the flexible sleeve around the proximal ring and shorten the length of the flexible sleeve between the proximal and distal rings.

11. The surgical wound protector of claim 10, wherein the proximal ring has a cross-sectional geometry comprising a height and a width, the height being greater than the width.

12. The surgical wound protector of claim 10, wherein the circumferential recesses in the medial and lateral surfaces are arcuate.

13. The surgical wound protector of claim 10, wherein the proximal ring is rollable between resting increments and the flip force is substantially the same between resting increments.

* * * * *